US00PP15011P3

(12) United States Plant Patent
Utecht

(10) Patent No.: US PP15,011 P2
(45) Date of Patent: Jul. 13, 2004

(54) GERANIUM PLANT NAMED'FISVITA'

(50) Latin Name: *Pelargonium zonale*
Varietal Denomination: Fisvita

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/715,543

(22) Filed: Nov. 19, 2003

(65) Prior Publication Data

US 2004/0073984 P1 Apr. 15, 2004

(30) Foreign Application Priority Data

Dec. 23, 2002 (CA) ..... PBR 02-3402

(51) Int. Cl.[7] ..... A01H 5/00

(52) U.S. Cl. ..... Plt./328

(58) Field of Search ..... Plt./238

*Primary Examiner*—Kent Bell
(74) *Attorney, Agent, or Firm*—Foley & Lardner LLP

(57) ABSTRACT

A new and distinct cultivar of geranium plant named 'Fisvita' particularly characterized by the combined features of light-salmon and white, semi-double flowers, early to mid season beginning of flowering, deep-green foliage with strong zonation, and medium sized plant habit, with a good proportion between the foliage canopy and the height of the inflorescences.

1 Drawing Sheet

Genus and Species of the Plant Claimed: Hybrid of the species *Pelargonium zonale* L'Héritier.
Variety Denomination: 'Fisvita'.

BACKGROUND OF THE INVENTION

The present invention comprises a new and distinct cultivar of geranium, botanically known as *Pelargonium zonale,* and hereinafter referred to by the cultivar name 'Fisvita'.

'Fisvita' is a product of a planned breeding program which had the objective of creating new zonal geranium cultivars with light salmon to light pink flower color, medium green, zoned foliage, and suitable for the range of medium sized varieties.

'Fisvita' originated from a hybridization made by the inventor, Angelika Utecht, in a controlled breeding program in Hillscheid, Germany, in 1992. The female parent was an unpatented hybrid seedling, no. 87-585-4, having single-type salmon colored flowers, medium green foliage with strong zonation, and moderately vigorous growth. The male parent of 'Fisvita' was the unpatented seedling no. 91-1009-1, with light salmon, semi-double flowers, large leaves with strong zonation, and compact plant habit.

'Fisvita' was selected as one flowering plant within the progeny of the stated cross by Angelika Utecht in 1993 in a controlled environment in Galdar, Gran Canaria, Spain.

The first act of asexual reproduction of 'Fisvita' was accomplished when vegetative cuttings were taken from the initial selection in the fall of 1993 in a controlled environment in Galdar, Gran Canaria, Spain, by, or under the supervision of, Angelika Utecht.

Horticultural examination of plants grown from cuttings of the plant initiated in May 1994, in Hillscheid, Federal Republic of Germany, and again from 2000 on, has demonstrated that the combination of characteristics as herein disclosed for 'Fisvita' are firmly fixed and are retained through successive generations of asexual reproduction.

'Fisvita' has not been observed under all possible environmental conditions. The phenotype may vary significantly with variations in environment such as temperature, light intensity and day length.

BRIEF SUMMARY OF THE INVENTION

The following observations, measurements, and comparisons describe plants grown in Hillscheid, Germany, under greenhouse conditions which approximate those generally used in commercial practice.

The following traits have been repeatedly observed and are determined to be basic characteristics of 'Fisvita' in combination distinguish this geranium as a new and distinct cultivar:

1. Light-salmon and white, semi-double flowers;
2. Relatively large inflorescences, well above the foliage;
3. Medium sized, rounded, medium-green leaves with strong zonation;
4. Medium sized and well-branched plant habit; and
5. Early to medium spring flowering response.

Of the many commercial cultivars known to the present inventor, the most similar in comparison to 'Fisvita' are the varieties 'Fisrolisa' (U.S. Plant Pat. No. 13,193), 'Americana Light Salmon' (U.S. Plant Pat. No. 7,936) and 'Designer Light Salmon' (unpatented).

In comparison to 'Fisrolisa', 'Fisvita' has a similar flower color, not quite as large leaves, stronger zonation, and somewhat less tall, about medium sized plant habit. In comparison to 'Americana Light Salmon', 'Fisvita' is not as tall and has somewhat smaller flowers and inflorescences. Furthermore, flowers of 'Americana Light Salmon' show a deeper shade of salmon in the middle of the flower, while the margins of petals are a similar hue as with flowers of 'Fisvita'. In comparison to 'Designer Light Salmon', 'Fisvita' has somewhat smaller flowers, and foliage with distinctly stronger zonation.

BRIEF DESCRIPTION OF THE DRAWING

The accompanying photographic drawing shows typical flower and foliage characteristics of 'Fisvita' with colors being as true as possible with an illustration of this type.

The photographic drawing shows a flowering potted plant of 'Fisvita'.

DETAILED BOTANICAL DESCRIPTION

In the following description color references are made to The Royal Horticultural Society Colour Chart. The color values were determined indoors from plants growing in a green-house in May 2003 in Hillscheid, Germany. The measurements were taken in Hillscheid, Germany, in mid-May, 11 weeks after planting of rooted cuttings. The plants were growing in 14 cm pots, they had not been pinched.

INFLORESCENCE

Umbel:

*Shape.*—Semi-spherical.
*Average diameter.*—111 mm.
*Average depth.*—70 mm.
*Peduncle length.*—173 mm.
*Peduncle color.*—Light green, RHS 143 C, occasionally with a slight tinge of brown, RHS 147 B.
*Pedicel.*—31 mm in length.
*Pedicel color.*—Mainly light green, RHS 144 B, in parts brownish infused, RHS 179 B.
*Number of flowers per umbel.*—About 60–80.

Corolla:

*Average diameter.*—48 mm.
*Form.*—Semi-double-type.
*Shape.*—Round outline, with the upper petals about the same size as the lower petals.
*Number of petals.*—7–9.
*Number of petaloids.*—None.
*Shape of petals.*—Obovate, base acute, upper end is truncate or rounded, margin is entire.
*Size of petals.*—Upper petals: 24–26 mm long, 18 mm wide; lower petals: 20–22 mm long, 19 mm wide.
*Color (general tonality from a distance of three meters)*.—Light salmon and white.
*Color of upper petals.*—Main part between RHS 41 C and 41 B, color near margin variable from RHS 56 A to 56 D.
*Markings of upper petals.*—No distinct markings.
*Color of lower petals.*—Main part between RHS 41 C and 41 B, color near margin variable from RHS 56 A to 56 D.
*Markings of lower petals.*—None.
*Color of lower surface of petals.*—Mainly RHS 56 D, in parts RHS 56 A.
*Color of sepals.*—Outer surface: light green, RHS 144 B; inner surface: light green, RHS 144 B.
*Number of sepals.*—5.
*Shape of sepals.*—Linear to lanceolate, acute tip, truncate base, surface with very short pubescence, margin entire.
*Size of sepals.*—9–11 mm long, 4 mm wide for the largest upper sepal, 2–3 mm in width for the other sepals.

Bud (just prior to petals unfolding):

*Shape.*—Elliptical.
*Color of sepals.*—Light green, RHS 143 C.
*Color of petals.*—RHS 38 C to 41 C, marbled.
*Length.*—13–14 mm.
*Width.*—8 mm.

REPRODUCTIVE ORGANS

Androecium.—2–5 fertile anthers, moderate pollen, yellow-orange, RHS 30 A, filaments white, RHS 155 D, to light-pink, RHS 52 D.
*Gynoecium.*—One pistil, whitish style, RHS 155 D to 65 D, stigma 5–6-lobed stigma, orange, RHS N30 A.
*Fertility/seed set.*—Occasionally, mainly in late summer to fall.
*Fruit.*—Oblong, about 6 mm wide, rostrum (beak) 38–42 mm long.
*Seed.*—Oblong, 4–5 mm long, brown RHS 177 B.

Spring flowering response period: In Hillscheid, Germany, in 2001 plants had on average 0.8 flowers opened 8 weeks after planting of rooted cuttings.

Outdoor flower production: Continuously and rich flowering, the flower count in 2003 in Hillscheid, Germany, indicated about 2.5–3 inflorescences per plant in mid May.

Durability: Good stability of flower color, no fading, fair rain resistance.

Lastingness of the individual flower: About 7–8 days at 18° C., about 16 days for the umbel.

Fragrance: None.

PLANT

Foliage:

*Shape.*—Kidney-shaped to nearly round, with cordate base, with the gap between the lowest lobes open, apex rounded with weak lobes, margin somewhat wavy.
*Margin.*—Bicrenate.
*Texture.*—Upper surface smooth, slightly glossy.
*Size of leaf.*—99 mm wide, 55 long.
*Color of upper surface.*—Medium green, approximately RHS 137 C.
*Color of zonation.*—Strong, brown, about RHS 166 A.
*Color of lower surface.*—RHS 137 D. Petioles: 75–95 mm long, 2.5–3.0 mm diameter, light green in color, approximately RHS 143 B.

General appearance and form:

*Stem color.*—Mainly light green, RHS 143 C; in places slightly brownish infused, RHS 147 B.
*Internode length.*—20 mm.
*Branching pattern.*—5–6 branches.
*Size of plants.*—19.6 cm tall, 29.5 cm wide (11-week-old plants, as described, measured from the top of the soil (base of the main stem) to the surface of the foliage canopy, without inflorescences).

I claim:

1. A new and distinct cultivar of geranium plant named 'Fisvita', as described and illustrated herein.

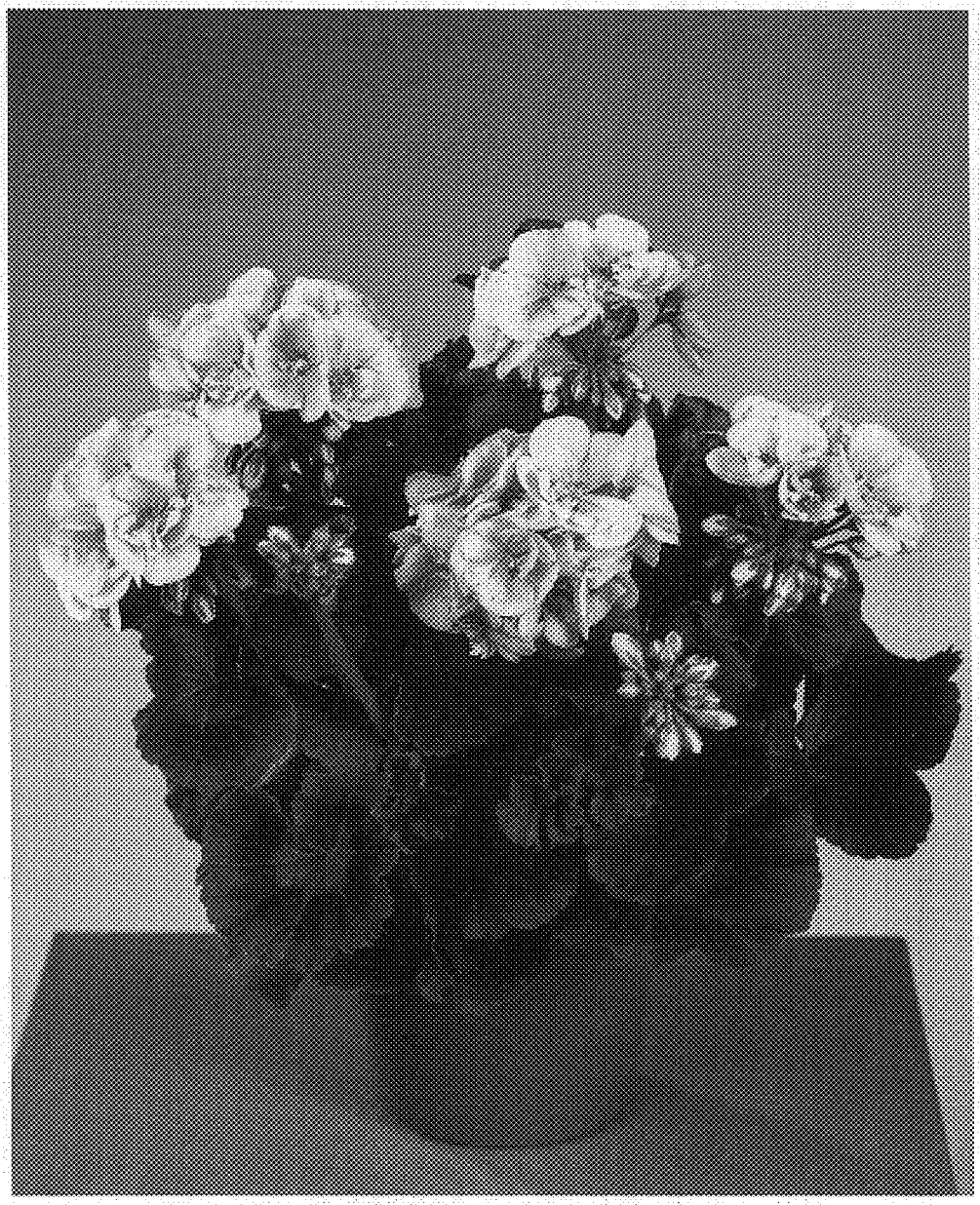

* * * * *